(12) United States Patent
Nelson et al.

(10) Patent No.: US 9,353,393 B2
(45) Date of Patent: May 31, 2016

(54) METHODS AND KITS FOR REDUCING NON-SPECIFIC NUCLEIC ACID AMPLIFICATION

(75) Inventors: John Richard Nelson, Clifton Park, NY (US); Gregory Andrew Grossmann, Halfmoon, NY (US); Robert Scott Duthie, Schenectady, NY (US); Sonali Jagdish Shah, Avon, CT (US); Ryan Charles Heller, Guilderland, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 210 days.

(21) Appl. No.: 13/446,474

(22) Filed: Apr. 13, 2012

(65) Prior Publication Data

US 2013/0210078 A1  Aug. 15, 2013

Related U.S. Application Data

(60) Provisional application No. 61/599,119, filed on Feb. 15, 2012.

(51) Int. Cl.
 C12Q 1/68 (2006.01)
 C12P 19/34 (2006.01)

(52) U.S. Cl.
 CPC ............ *C12P 19/34* (2013.01); *C12Q 1/6848* (2013.01); *C12Q 1/6853* (2013.01); *C12Q 2525/113* (2013.01); *C12Q 2525/179* (2013.01); *C12Q 2525/204* (2013.01); *C12Q 2527/107* (2013.01)

(58) Field of Classification Search
 CPC ......................... C12Q 1/6848; C12Q 2527/101
 USPC ........................................................ 435/91.2
 See application file for complete search history.

(56) References Cited

U.S. PATENT DOCUMENTS

| | | | |
|---|---|---|---|
| 7,074,600 | B2 | 7/2006 | Dean et al. |
| 7,176,002 | B2 | 2/2007 | Lao et al. |
| 7,993,839 | B2* | 8/2011 | Nelson et al. ............... 435/6.12 |
| 8,222,389 | B2 | 7/2012 | Venema |
| 2003/0165859 | A1* | 9/2003 | Nazarenko et al. ............ 435/6 |
| 2004/0086880 | A1* | 5/2004 | Sampson et al. ............... 435/6 |
| 2007/0281308 | A1 | 12/2007 | Zon et al. |
| 2009/0130720 | A1* | 5/2009 | Nelson et al. ............... 435/91.2 |
| 2009/0176280 | A1 | 7/2009 | Hutchison, III et al. |
| 2009/0191553 | A1 | 7/2009 | Hendrickson |
| 2011/0086354 | A1 | 4/2011 | Tzubery et al. |
| 2011/0195457 | A1 | 8/2011 | Nelson et al. |

FOREIGN PATENT DOCUMENTS

| | | |
|---|---|---|
| WO | 0242490 A1 | 5/2002 |
| WO | 2009004630 A1 | 1/2009 |
| WO | 2010021702 A1 | 2/2010 |

OTHER PUBLICATIONS

Levin JD, Fiala D, Samala MF, Kahn JD, Peterson RJ. Position-dependent effects of locked nucleic acid (LNA) on DNA sequencing and PCR primers. Nucleic Acids Res. 2006;34(20):e142.*
Hughesman et al., "Stability and Mismatch Discrimination of DNA Duplexes containing 2,6-Diaminopurine and 2-Thiothymidine Locked Nucleic Acid Bases", Nucleic acids Symposium Series, vol. 52, pp. 245-246, 2008.
"Custom Oligonucleotides", Eurogentec Catalogue, pp. 34-97, 2009-2010.
International Search Report for Application No. PCT/US2013-026136 (ISA/210) mailed Apr. 25, 2013; 1 page.
Detter, J.C., et al., "Isothermal strand-displacement amplification applications for high-throughput genomics", Genomics, Academic Press, San Diego, US, vol. 80, No. 6, Dec. 2002, pp. 691-698.
Latorra, D., et al., "Design considerations and effects of LNA in PCR primers", Molecular and Cellular Probes, Academic Press, London, GB, vol. 17, No. 5, Oct. 2003, pp. 253-259.
EPO Search and Written Opinion issued in connection with corresponding EP Application No. 13749671.7 dated Aug. 6, 2015.
Singh, Sanjay et al., "LNA (locked nucleic acids): synthesis and high-affinity nucleic acid recognition" Chem. Commun., 1998, pp. 455-456.
Hoshika, Shuichi, et al., "Artificial Genetic Systems: Self-Avoiding DNA in PCR and Multiplexed PCR" Angewandte Chem. Int. Edition, Jul. 26, 2010, vol. 49, Issue 32, pp. 5554-5557.
Koshkin, A. A. et al., "LNA (locked nucleic acids):Synthesis of the Adenine, Cytosine, Cuanine, 5-Methylcytosine, Thymine and Uracil Bicyclonucleoside Monomers, Oligomerisation, and Unprecedented Nucleic Acid Recognition", Tetrahedron, 1998, vol. 54, pp. 3607-3630.

* cited by examiner

*Primary Examiner* — Angela M Bertagna
*Assistant Examiner* — Olayinka Oyeyemi
(74) *Attorney, Agent, or Firm* — Fletcher Yoder, P.C.

(57) ABSTRACT

Methods and kits for efficient amplification of nucleic acids are provided. The disclosure generally relates to methods and kits for nucleic acid amplification of target nucleic acids of interest. The methods described herein promote the synthesis of the target nucleic acid (i.e., template nucleic acid) by reducing the production of undesirable primer-dimer structures and chimeric nucleic acid products during the amplification process by using novel modified primers.

6 Claims, 8 Drawing Sheets

Standard A-T base pair

Modified oligos form very unstable pairs with each other

However, 2-amino-A forms even more stable pairs with unmodified input DNA

*Fig. 1*

DESCRIPTION OF FORMULATIONS

| | Enzymatic Cleaning Reaction | Final [Salt] In Reaction | Random Hexamer |
|---|---|---|---|
| GenomiPhi | No | 75 mM | NNNN*N*N |
| Clean GPhi | Yes | 75 mM | NNNN*N*N |
| SD GPhi | Yes | 15 mM | +W+WNNN*S |
| AT GPhi | Yes | 15 mM | +N+N(atN)(atN)*N |

\* represents phosphorothioate linkage

\+ precedes an LNA base
W = A or T
S = C or G (atN) is a mixture of random bases in which:
2-amino-A is substituted for A
2-thio-T is substituted for T
(will not pair with each other)

+N+N(atN)(atN)*N
LNA

*Fig. 6B*    16S PCR

Fig. 6C

METHODS AND KITS FOR REDUCING NON-SPECIFIC NUCLEIC ACID AMPLIFICATION

CROSS-REFERENCE TO RELATED APPLICATIONS

This application claims the benefit of U.S. Provisional Application No. 61/599,119, filed on Feb. 15, 2012, which is herein incorporated by reference in its entirety.

FIELD OF THE INVENTION

The disclosure generally relates to methods and kits for the amplification of target nucleic acids of interest. The methods and compositions described herein promote the amplification of the desired target nucleic acid through the use of novel primers, thereby reducing the production of undesirable amplification products (e.g., primer-dimers and chimeric nucleic acids).

BACKGROUND

A variety of techniques are currently available for efficient amplification of nucleic acids even from a few molecules of a starting nucleic acid template. These include polymerase chain reaction (PCR), ligase chain reaction (LCR), self-sustained sequence replication (3SR), nucleic acid sequence based amplification (NASBA), strand displacement amplification (SDA), multiple displacement amplification (MDA), and rolling circle amplification (RCA). Many of these techniques involve an exponential amplification of the starting nucleic acid template and are able to generate a large number of amplified products quickly. Kits for the amplification of a target nucleic acid are commercially available (e.g., GenomiPhi™ (General Electric, Inc.) and RepliG™ (Qiagen, Inc.), but improvements to these methods would be advantageous.

Nucleic acid amplification techniques are often employed in nucleic acid-based assays used for analyte detection, sensing, forensic and diagnostic applications, genome sequencing, whole-genome amplification, and the like. Such applications often require amplification techniques having high specificity, sensitivity, accuracy, and robustness. Most of the currently available techniques for nucleic acid amplification, however, suffer from high background signals, which are generated by non-specific amplification reactions yielding unwanted amplification products. These non-specific amplification reactions hinder effective utilization of many of these techniques in critical nucleic acid-based assays. For example, use of a traditional amplification reaction may produce a false-positive result, thereby leading to an incorrect diagnosis. Such non-specific, background amplification reactions become even more problematic when only trace amounts of the target nucleic acid to be amplified are available (e.g., whole-genome amplification from a single DNA molecule).

Non-specific, background amplification reactions may be due to, for example, amplification of a contaminating nucleic acid sequence in the sample, primer-dimer formation, or production of chimeric nucleic acids (e.g., resulting from self-hybridization of the desired nucleic acid products). A frequent source of non-specific amplification in a nucleic acid amplification reaction results from various undesirable primer interactions. A primer may hybridize to regions of a nucleic acid in either a target nucleic acid or in a contaminating nucleic acid that share some homology with a portion of the target nucleic acid. If the 3' end of a primer has sufficient homology to an untargeted region, this region may be amplified.

Non-specific amplification may also result from unintended nucleic acid template-independent primer-primer interactions. Primers may form primer-dimer structures by intra- or inter-strand primer annealing (e.g., intra-molecular or inter-molecular hybridizations), resulting in amplification of unwanted nucleic acids. The resultant spurious primer extension products may be further amplified and may at times predominate, inhibit, or mask the desired amplification of the targeted sequence. Moreover, the amplification products may self-hybridize, allowing the nucleic acid polymerase to generate hybrid products or chimeric products during the amplification reaction.

For priming DNA synthesis, current MDA formulations often utilize random hexamers with the sequence 5'-NNNNN*N, where "N" represents a deoxyadenosine (dA), deoxycytidine (dC), deoxyguanosine (dG), or deoxythymidine (dT) and "*" represents a phosphorothioate linkage.

Constrained-randomized hexamer primers that cannot cross-hybridize via intra- or inter-molecular hybridization (e.g., $R_6$, where R=A/G) have been used for suppressing primer-dimer structure formation during nucleic acid amplification. These constrained-randomized primers, however, impart considerable bias in nucleic acid amplification reaction. Such primers are also of limited use for sequence-non-specific or sequence-non-biased nucleic acid amplification reactions (e.g., whole genome or unknown nucleic acid sequence amplification).

For priming DNA synthesis, MDA formulations frequently utilize random hexamers with the sequence 5'-NNNNN*N, where "N" represents a deoxyadenosine (dA), deoxycytidine (dC), deoxyguanosine (dG), or deoxythymidine (dT) and "*" represents a phosphorothioate linkage. One solution to minimizing competing non-target nucleic acid (i.e., template DNA) amplification is to modify the oligonucleotide primers in such a way as to inhibit their ability to anneal with one another.

Previous research to overcome the issues associated with nucleic acid amplification using random hexamer primers described above includes those methods and kits disclosed in U.S. Pat. No. 7,993,839 (issued Aug. 9, 2011). The techniques described in this patent include but are not limited to the use of primers that are hexamers of the general structure 5'-+W+WNNN*S-3', where "+" precedes a locked nucleic acid base (i.e., "an LNA base"; for example, +A=an adenosine LNA molecule), "W" represents a mixture of only dA and dT, and "S" represents a mixture of only dC and dG. The "*" represents a phosphorothioate linkage between the two nucleotides. Since "W" bases are unable to stably pair with "S" bases, the formation of the oligonucleotide duplex is inhibited, which leads to decreased amplification of non-template nucleic acids. These methods and kits may be referred to as "SD GenomiPhi."

One improvement to the speed and sensitivity of MDA when amplifying trace nucleic acid samples is the incorporation of LNAs into the oligonucleotide primers. LNAs are a class of conformationally restricted nucleotide analogues that serve to increase the speed, efficiency, and stability of base pairing, thereby promoting the hybridization of the modified oligonucleotides to their target sequences in the nucleic acid of interest. For each LNA monomer incorporated into an oligonucleotide primer, the duplex melting temperature ($T_m$) is increased by 2-8° C. The increase in $T_m$ of the duplex allows the MDA reaction to be performed under more stringent conditions, such as at a higher temperature or with a lower concentration of salt (e.g., 15 mM KCl as opposed to the 75 mM KCl used in traditional amplification reactions with unmodified primers). While the kinetics of amplification using MDA are dramatically increased by incorporation of LNAs into the random primers, one drawback is that the hexamers also anneal to each other more efficiently, leading to amplification of unwanted nucleic acids (e.g., primer-dimers).

The problems associated with the undesirable amplification of non-target nucleic acids have also been approached from the standpoint of removing contaminating nucleic acids from reagents and reagent solutions used in nucleic acid amplification methods. Kits and methods for generating nucleic acid contaminant-free reagents and reagent solutions for use in nucleic acid amplification are disclosed in U.S. Patent Application Publication No. 2009/0155859. Such methods include processing of polymerase solutions, nucleotide solutions, and primer solutions to render contaminating nucleic acids inert. The methods employ the proofreading activity of the polymerase and/or exonucleases to decontaminate the reagents and reagent solutions. The methods described in U.S. Patent Application Publication No. 2009/0155859 may at times be referred to as "Clean GenomiPhi" or "Clean GPhi."

Despite these advancements, there remains a need for developing more efficient nucleic acid amplification methods that have lower bias in terms of sequence coverage and produce lower levels of non-specific, background amplification. Development of primers for nucleic acid amplification without sequence bias that also reduce primer-primer interaction and minimize the production of chimeric nucleic acids (e.g., unwanted nucleic acid products resulting from the annealing of the hexamer primers to the target nucleic acid amplification products) is needed in the art.

BRIEF DESCRIPTION

The present application provides methods and compositions for amplification of target nucleic acids. Without intending to be limited to a particular mechanism of action, the methods disclosed herein are believed to more efficiently amplify the desired target nucleic acid (e.g., "DNA template" or "nucleic acid template") through the use of modified primers designed to minimize or prevent the production of unwanted primer-dimers and chimeric products observed with other nucleic acid amplification methods and kits. The methods described herein utilize a novel primer design method to avoid the production of spurious nucleic acid amplification products. For example, in one embodiment random hexamers comprising 2-amino-deoxyadenosine (2-amino-dA) and 2-thio-deoxythymidine (2-thio-dT) are produced and used in a nucleic acid amplification reaction (e.g., MDA). The methods and kits described herein may be referred to as "AT GenomiPhi."

In one aspect of the invention, these modified hexamers are of the general formula: +N+N(atN)(atN)(atN)*N, wherein "+" precedes an LNA base, as described above, and (atN) represents a random mixture of 2-amino-dA, dC, dG, and 2-thio-dT. The hexamers used in another aspect of this disclosure comprise: (atN)(atN)(atN)(atN)(atN)*N, wherein the notations are consistent between these two hexamer designs. As described in greater detail below, the use of these hexamers in nucleic acid amplification techniques addresses the minimizes or eliminates the problems associated with the production of primer-dimer formation and chimeric nucleic acids observed in traditional methods by inhibiting the ability of the random hexamers to anneal with one another, by increasing the melting $T_m$ of the primers, improving the binding efficiency of the hexamer to the target nucleic acid via the addition of LNAs and 2-amino-dA to the primers, and preventing annealing of the target DNA to itself through the incorporation of 2-thio-dT into the random hexamers. Moreover, these primer modifications, which increase their binding strength to the target nucleic acid, permit the utilization of more stringent hybridization buffers that further minimize the likelihood of the production of primer-dimers and chimeric nucleic acid products.

DRAWINGS

These and other features, aspects, and advantages of the chemically modified porous membranes will become better understood when the following detailed description is read with reference to the accompanying drawings in which like characters represent like parts throughout the drawings, wherein:

FIG. 4A provides the results of whole *Bacillus subtilis* genome amplification reactions from the indicated amounts of chromosomal DNA. A no template control was also performed (NTC). Details are set forth in Example 3 below. The legend for this figure is as follows: 1) solid line open square: NNNN*N*N (where * indicates a phosphorothioate linkage), 2) solid line solid triangle: (atN)(atN)(atN)(atN)*(atN)*N (where a mixture of random bases in which: 2-amino-A is substituted for A, 2-thio-T is substituted for T), 3) solid line open triangle: +N+N+N+N+N*, 4) dotted line open diamond +N+N(atN)(atN)(atN)*N, 5) solid line open circle: WWN+N+N*S, and 6) solid line solid circle +W+WNNN*S.

DETAILED DESCRIPTION

Nucleic acid-based assays involving single molecule DNA amplification or whole-genome amplification demand highly efficient nucleic acid amplification methods that have high yield, high fidelity and have little bias in terms of sequence coverage. A variety of methods that are currently available for use include, but are not limited to, polymerase chain reaction (PCR), ligase chain reaction (LCR), self-sustained sequence replication (3SR), nucleic acid sequence based amplification (NASBA), strand displacement amplification (SDA), and rolling circle amplification (RCA). Isothermal nucleic acid amplification reactions such as rolling circle amplification (RCA), or multiple displacement amplification (MDA) employing random primers are more adaptable than temperature-dependent nucleic acid amplification reaction (e.g., PCR) for such applications. However, these methods often yield a dominant background signal due to undesired non-specific nucleic acid amplification reactions, especially when the concentration of target nucleic acid template is low (e.g., below 1 ng).

Figure 1:
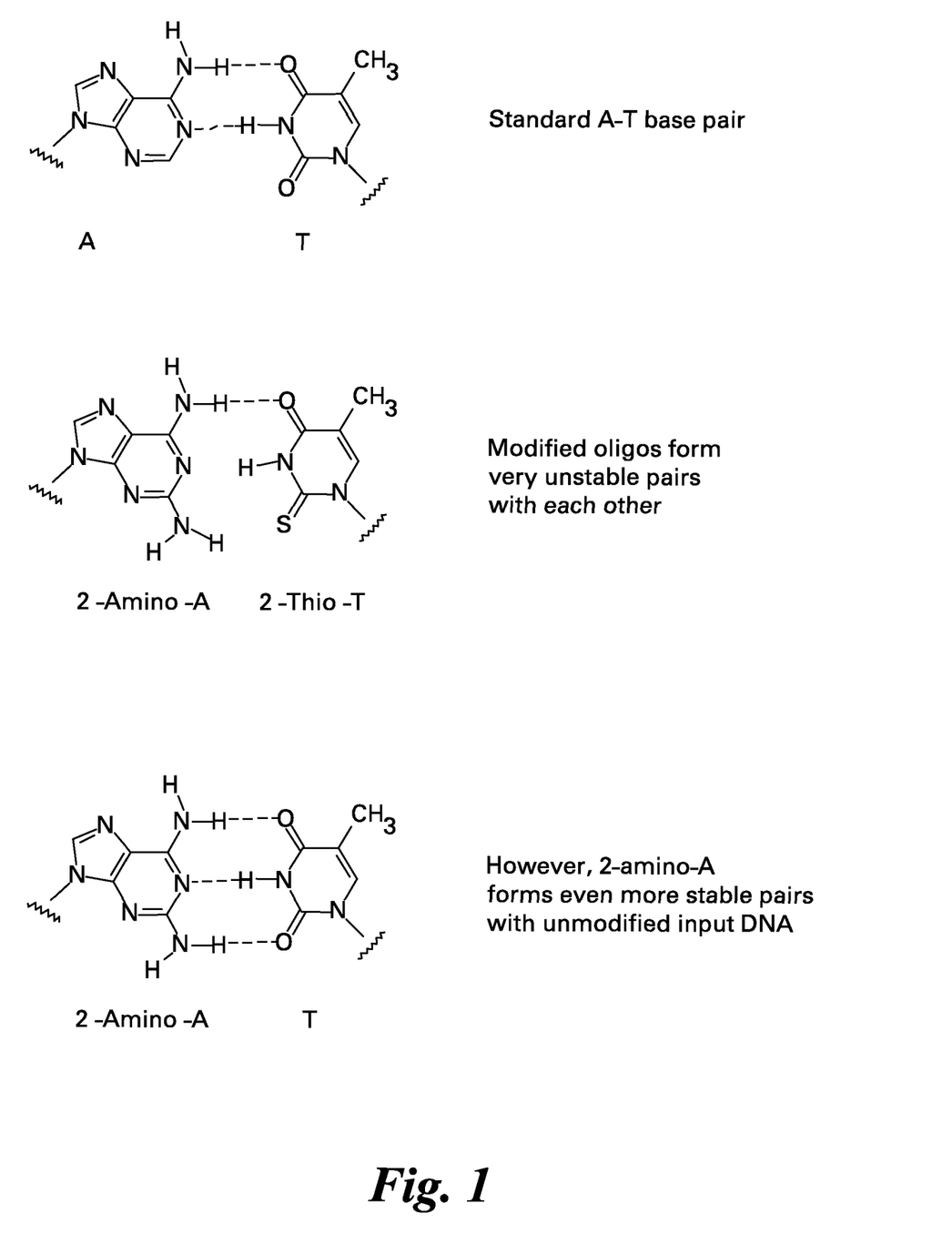
FIG. 1 depicts the base pairing combination of: 1) 2-amino-deoxyadenosine (2-amino-dA) and 2-thio-deoxythymidine (2-thio-dT) and 2) 2-amino-dA and unmodified T. While the 2-amino-dA/2-thio-dT pairing is very unstable, the 2-amino-dA/T pairing is actually more stable than a standard A/T pairing.
Figure 2:
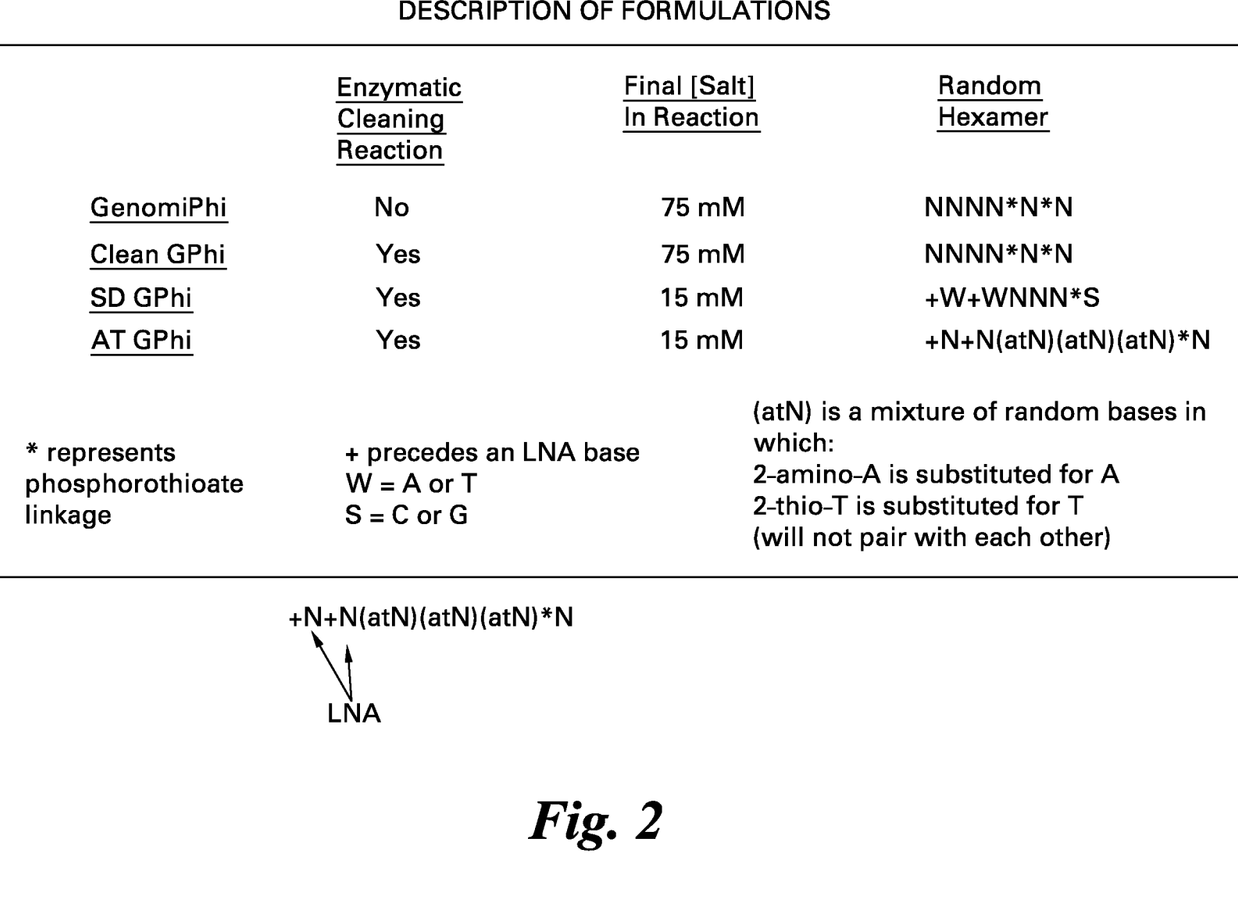
FIG. 2 depicts the improvements to the standard GenomiPhi™ formulation were the addition of the enzymatic cleaning reaction, adjustment of the potassium chloride concentration, and the composition of the random hexamer oligonucleotide. The abbreviations used in this figure are as follows: N=random base; *=phosphorothioate linkage; +, precedes LNA base; W=only the bases A or T; S=only the bases C or G.

The methods and kits described herein are intended to efficiently amplify target nucleic acids with the additional advantage of reducing non-specific amplification of non-target nucleic acids (e.g., primer-dimers, chimeric nucleic acid products, etc.) that are observed with other methods of nucleic acid amplification. Without intending to be limited to a particular mechanism of action, the disclosed methods accomplish these goals by the incorporation of nucleotide analogue bases that increase $T_m$ (e.g., the inclusion of each 2-amino-dA base in the hexamer increases the $T_m$ by approximately 3° C.) or prevent undesirable primer-dimer formation. In certain embodiments, 2-amino-deoxyadenosine (2-amino-dA), 2-thio-deoxythymidine (2-thio-dT), or other nucleotide analogues of interest are incorporated into the random hexamers used for amplification of the target nucleic acid. As shown in FIG. 1, nucleotide analogues bases do not stably pair with each other due to steric hindrance (e.g., 2-amino-dA forms only one hydrogen bond with 2-thio-dT as opposed to the three hydrogen bonds observed with the unmodified dA and dT), formation of unwanted nucleic acid duplexes is significantly reduced, thereby leading to the overall inhibition of non-target nucleic acid amplification. In fact, the inclusion of these nucleotide analogue bases actually improves the ability of the primers to hybridize to the target nucleic acid because 2-amino-dA forms three hydrogen bonds with unmodified deoxythymidine (dT) and, similarly, 2-thio-dT forms a normal stable pair with its unmodified partner (i.e., deoxyadenosine (dA)).

When combined with one or more LNA nucleotides, the methods set forth herein produce even more robust results. For each LNA nucleotide incorporated into an oligonucleotide primer, increases the $T_m$ by 2-8° C. The use of the modified nucleotides analogues bases and LNA nucleotides also permits the use of more stringent hybridization buffers, thereby further decreasing the production of unwanted non-target nucleic acid amplification. Moreover, higher temperatures and lower salt concentrations can also be used in the nucleic acid amplification reaction to facilitate the amplification of specific target nucleic acids of interest.

Definitions

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural references unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein, the term "nucleoside" refers to a glycosylamine compound wherein a nucleic acid base (e.g., nucleobase) is linked to a sugar moiety. The nucleic acid base may be a natural nucleobase or a modified or synthetic nucleobase. The nucleic acid base includes, but is not limited to, a purine base (e.g., adenine or guanine), a pyrimidine (e.g., cytosine, uracil, or thymine), or a deazapurine base. The nucleic acid base may be linked to the 1' position, or at an equivalent position of a pentose (e.g., a ribose or a deoxyribose) sugar moiety. The sugar moiety includes, but is not limited to, a natural sugar, a sugar substitute (e.g., a carbocyclic or an acyclic moiety), a substituted sugar, or a modified sugar (e.g., bicyclic furanose unit as in LNA nucleotide). The nucleoside may contain a 2'-hydroxyl, 2'-deoxy, or 2',3'-dideoxy forms of the sugar moiety.

As used herein the terms "nucleotide" or "nucleotide base" refer to a nucleoside phosphate. It includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP) or a ribonucleoside triphosphate (NTP). The nucleotides may be represented using alphabetical letters (letter designation), as described in Table 1. For example, A denotes adenosine (i.e., a nucleotide containing the nucleobase, adenine), C denotes cytosine, G denotes guanosine, and T denotes thymidine. W denotes either A or T/U, and S denotes either G or C. N represents a random nucleotide (i.e., N may be any of A, C, G, or T/U). A plus (+) sign preceding a letter designation denotes that the nucleotide designated by the letter is a LNA nucleotide. For example, +A represents an adenosine LNA nucleotide, and +N represents a locked random nucleotide (a random LNA nucleotide). A star (*) sign preceding a letter designation denotes that the nucleotide designated by the letter is a phosphorothioate modified nucleotide. For example, *N represents a phosphorothioate modified random nucleotide.

As used herein, the term "nucleotide analogue" refers to modified compounds that are structurally similar to naturally occurring nucleotides. The nucleotide analogue may have an altered phosphorothioate backbone, sugar moiety, nucleobase, or combinations thereof. Generally, nucleotide analogues with altered nucleobases confer, among other things, different base pairing and base stacking proprieties. Nucleotide analogues having altered phosphate-sugar backbone (e.g., PNA, LNA, etc.) often modify, among other things, the chain properties such as secondary structure formation. At times in the instant application, the terms "nucleotide analogue," "nucleotide analogue base," "modified nucleotide base," or "modified base" may be used interchangeably.

Any nucleotide analogue that minimizes or prevents the amplification of a non-target nucleic acid may be used in the practice of the invention. In addition to those nucleotide analogues described above, a variety of nucleotide analogues with the desired abilities are well known to those of skill in the art. See, for example, U.S. Pat. No. 5,912,340; International Publication No. WO 2010/021702; and Hoshika et al. (2010) *Angew. Chem. Int. Ed.* 49:5554-5557, all of which are herein incorporated by reference in their entirety. Such nucleotide analogues include but are not limited to "self-avoiding molecular recognition systems" (SAMRS). SAMRS as described by Hoshika et al. are based on 2-thiothymine, 2-aminopurine, hypoxanthine, and N4-ethylcytosine as T*, A*, G*, and C*. When these are introduced individually into a reference DNA duplex, the corresponding SAMRS:standard pairs contributed to duplex stability to the same extent as an A:T pair. The SAMRS:SAMRS pair contributed less to the stability of the reference duplex than the corresponding SAMRS:standard pair. Hoshika et al. (2010) *Angew. Chem. Int. Ed.* 49:5554-5557.

TABLE 1

Letter designations of various nucleotides

| Symbol Letter | Nucleotide |
| --- | --- |
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998.)). The 2' and 4' position of the furanose unit in the LNA nucleotide may be linked by an O-methylene (e.g., oxy-LNA: 2'-O, 4'-C-methylene-β-D-ribofuranosyl nucleotide), an S-methylene (thio-LNA), or a NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations.

As used herein, the term "oligonucleotide" refers to oligomers of nucleotides or derivatives thereof. The term "nucleic acid" as used herein refers to polymers of nucleotides or derivatives thereof. A "target nucleic acid or "nucleic acid template" means the particular sequence that is intended and desired to be amplified. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides/nucleic acids may be a DNA, an RNA, or their analogues (e.g., a phosphorothioate analogue). The oligonucleotides or nucleic acids may also include modified bases, and/or backbones (e.g., a modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide. The nucleotide adjacent to the terminal nucleotide refers to a nucleotide that is located at a penultimate position from the terminal position.

As used herein, the term "primer", or "primer sequence" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or nucleotide analogues (e.g., those that increase $T_m$). Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long. The "oligonucleotide primers" used in the methods of amplification of a target nucleic acid described herein will be of a length appropriate for a particular set of experimental conditions. The determination of primer length is well within the routine capabilities of those of skill in the art. In certain embodiments described in the instant application the oligonucleotide primer is a hexamer, more particularly a hexamer comprising at least one nucleotide analogue that increases $T_m$ and/or prevents primer-dimer formation. The primers of the present disclosure may further include an LNA nucleotide base.

As used herein, the term "random primer" or "complete random primer" refers to a mixture of primer sequences, generated by randomizing a nucleotide at any given location in an oligonucleotide sequence in such a way that the given location may consist of any of the possible nucleotides or their analogues (e.g., complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown.

As described herein, "partially constrained primer" refers to a mixture of primer sequences, generated by completely randomizing some of the nucleotides of an oligonucleotide sequence (i.e., the nucleotide may be any of A, T/U, C, G, or their analogues) while restricting the complete randomization of some other nucleotides (i.e., the randomization of nucleotides at certain locations are to a lesser extent than the possible combinations A, T/U, C, G, or their analogues). For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As described herein, the term "partially constrained primer having a terminal mismatch primer-dimer structure" refers to a partially constrained primer sequence, wherein when two individual primer sequences in the partially constrained primer hybridize each other inter-molecularly, with an internal homology of three or more nucleotides, to form a primer-dimer structure having no recessed ends, or a primer-dimer structure having a single-nucleotide base 3' recessed ends, or a primer-dimer structure having a two-nucleotide base 3' recessed ends, there exists a nucleotide mismatch (i.e., nucleotides do not base-pair) at both the 3' terminal nucleotides in the primer-dimer structure. For example, a partially constrained pentamer primer represented by WNNNS provides a terminal mismatch at both the 3' terminal nucleotides when it is inter-molecularly hybridized to form a primer-dimer structure having no recessed ends. In the primer-dimer structure, there exists an internal homology of three nucleotides (i.e., the three random nucleotides in WNNNS may base-pair with each other when the primer-dimer structure having no recessed ends is formed by inter-molecular hybridization). However, this primer example does not provide a terminal mismatch when it is inter-molecularly hybridized to form a primer-dimer structure with single-nucleotide base 3' recessed ends. Similarly, a partially constrained hexamer primer represented by WWNNNS provides a terminal mismatch at both the 3' terminal nucleotides when it is inter-molecularly hybridized to form a primer-dimer structure having no recessed ends. Moreover, this primer example provides a terminal mismatch at both the 3' terminal nucleotides even when it is inter-molecularly hybridized to form a primer-dimer structure having a single-nucleotide base 3' recessed ends. A partially constrained heptamer primer represented by WWWNNNS provides a terminal mismatch at both the 3' terminal nucleotides when it is inter-molecularly hybridized to form a primer-dimer structure having no recessed ends. Further, this primer example provides a terminal mismatch at both the 3' terminal nucleotides when it is inter-molecularly hybridized to form a primer-dimer structure having a single-nucleotide base 3' recessed ends, or to form a primer-dimer structure having a two-nucleotide base 3' recessed ends.

As used herein, the term "plasmid" refers to an extra-chromosomal nucleic acid that is separate from a chromosomal nucleic acid. A plasmid DNA may be capable of replicating independently of the chromosomal nucleic acid (chromosomal DNA) in a cell. Plasmid DNA is often circular and double-stranded.

As used herein, the terms "amplification", "nucleic acid amplification", or "amplifying" refer to the production of multiple copies of a nucleic acid template, or the production of multiple nucleic acid sequence copies that are complementary to the nucleic acid template. These terms may be used interchangeably in this application.

As used herein, the term "target nucleic acid" refers to a nucleic acid that is desired to be amplified in a nucleic acid amplification reaction. For example, the target nucleic acid comprises a nucleic acid template.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction, the DNA polymerase needs a primer to which it can add the first nucleotide. Suitable primers comprise oligonucleotides of RNA or DNA. The DNA polymerases may be a naturally occurring DNA polymerases or a variant of natural enzyme having the above-mentioned activity. For example, it may include a DNA polymerase having a strand displacement activity, a DNA polymerase lacking 5'→3' exonuclease activity, a DNA polymerase having a reverse transcriptase activity, or a DNA polymerase having an endonuclease activity.

As used herein the term "proofreading DNA polymerase" refers to any DNA polymerase that is capable of correcting its errors while performing DNA synthesis. A proofreading DNA polymerase possesses a 3'→5' exonuclease activity apart from its polymerase activity, and this exonuclease activity is referred as proofreading activity. Proofreading activity of such polymerases correct mistakes in the newly synthesized DNA. During DNA synthesis, when an incorrect base pair is recognized, the proofreading DNA polymerase reverses its direction by one base pair of DNA. The 3'→5' exonuclease activity (proofreading activity) of the enzyme allows the incorrect nucleotide base pair to be excised. Following the nucleotide base excision, the polymerase re-inserts the correct nucleotide base, and continues the DNA synthesis. When free dNTPs are present in the solution or reaction mixture suitable for DNA synthesis, the primary activity of the proofreading DNA polymerase is DNA synthesis. However, when dNTPs are not available for the DNA synthesis reaction, the primary activity of the proofreading DNA polymerase may be its 3'→5' exonuclease activity. Some of the proofreading DNA polymerases may require the presence of a divalent cation for their proofreading activity as well as for their polymerase activity. Suitable divalent cations that can switch on the proofreading activity of the proofreading polymerases include, but are not limited to, magnesium or manganese.

As used herein, "a strand displacing nucleic acid polymerase" refers to a nucleic acid polymerase that has a strand displacement activity apart from its nucleic acid synthesis activity. That is, a strand displacing nucleic acid polymerase can continue nucleic acid synthesis on the basis of the sequence of a nucleic acid template strand (i.e., reading the template strand) while displacing a complementary strand that had been annealed to the template strand.

As used herein, the term "complementary," when used to describe a first nucleic acid/oligonucleotide sequence in relation to a second nucleic acid/oligonucleotide sequence, refers to the ability of a oligonucleotide comprising the first nucleic acid/oligonucleotide sequence to hybridize (e.g., to form a duplex structure) under certain hybridization conditions with an oligonucleotide comprising the second nucleic acid/oligonucleotide sequence. Hybridization occurs by base pairing of nucleotides (complementary nucleotides). Base pairing of the nucleotides may occur via Watson-Crick base pairing, non-Watson-Crick base pairing, or base pairing formed by non-natural/modified nucleotides.

As used herein the term "high stringency hybridization conditions" or "high stringent hybridization conditions" refer to conditions that impart a higher stringency to an nucleic acid hybridization event than the stringency provided by conditions that are generally used for nucleic acid amplification reactions. For example, a high stringency hybridization condition may be accomplished in a nucleic acid amplification reaction by increasing the reaction temperature or by decreasing the salt concentration. Nucleic acid amplification reactions containing short primers are often carried out at about 75 mM salt concentration. In contrast, a nucleic acid amplification reaction performed at about 15 mM salt concentration may represent a high stringency hybridization condition. High stringency hybridization condition may be provided in an in-vitro isothermal nucleic acid amplification reaction by increasing the temperature from about 30° C., which is often used. For example, the isothermal nucleic acid amplification reaction may be performed at about 35° C. to about 45° C. to provide a high stringency hybridization condition.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction may be initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatamers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase.

As used herein, multiple displacement amplification (MDA) refers to a nucleic acid amplification method, wherein the amplification involves the steps of annealing primers to a denatured nucleic acid followed by a strand displacement nucleic acid synthesis. As nucleic acid is synthesized by strand displacement, a gradually increasing number of priming events occur, forming a network of hyper-branched nucleic acid structures. MDA is highly useful for whole-genome amplification for generating high-molecular weight DNA with limited sequence bias from a small amount of genomic DNA sample. Strand displacing nucleic acid polymerases such as Phi29 DNA polymerase or large fragment of the Bst DNA polymerase may be used in multiple displacement amplification. MDA is often performed under isothermal reaction conditions, and random primers are used in the reaction for achieving amplification with limited sequence bias.

As used herein the term "reaction mixture" refers to the combination of reagents or reagent solutions, which are used to carry out a chemical analysis or a biological assay. In some embodiments, the reaction mixture comprises all necessary components to carry out a nucleic acid (DNA) synthesis/amplification reaction.

As used herein, the terms "reagent solution" or "solution suitable for performing a DNA synthesis reaction" or "amplification solution" refer to any or all solutions, which are typically used to perform an amplification reaction or DNA synthesis. They include, but are not limited to, solutions used in isothermal DNA amplification methods, solutions used in PCR amplification reactions, or the like. The solution suitable for DNA synthesis reaction may comprise buffer, salts, and/or nucleotides. It may further comprise primers and/or a DNA template to be amplified.

In some embodiments, kits for nucleic acid amplification are provided. The kits contain reagents, packaged together, that are required to practice the presently described methods of nucleic acid amplification. In one embodiment, the kit comprises a nucleic acid polymerase, the nucleotide analogues described above (e.g., 2-amino-dA and 2-thio-dT), and LNA bases. The nucleic acid polymerase and the other reagents may be packaged in a single vessel or they may be packaged in separate vessels.

In one embodiment, the kit comprises a Phi29 DNA polymerase and a partially constrained primer having a terminal mismatch primer-dimer structure, packaged together. The partially constrained primer in the kit may comprise a nucleotide analogue, such as a LNA nucleotide. In some embodiments, the partially constrained primer is a DNA-LNA chimera primer. The partially constrained primer in the kit may be a nuclease-resistant primer, for example, an exonuclease-resistant primer. These exonuclease-resistant primers in the kit may contain one or more phosphorothioate linkages between the nucleotides. In one embodiment, the kit comprises 5'-+W+WNNN*S-3', where "+" precedes a locked nucleic acid base (i.e., "an LNA base"; for example, +A=an adenosine LNA molecule and similarly for the other nucleotides), "W" represents a mixture of only dA and dT, "S" represents a mixture of only dC and dG, the "*" represents a phosphorothioate linkage between the two nucleotides, and a Phi29 DNA polymerase.

In a further embodiment, the kit comprises random hexamers for performing the GenomiPhi AT methods described herein. Specifically, such kits comprise modified hexamers are of the general formula: +N+N(atN)(atN)(atN)*N, wherein "+" precedes an LNA base, as described above, and (atN) represents a random mixture of 2-amino-dA, dC, dG, and 2-thio-dT. Alternatively, these kits may comprise hexamers represented by the formula (atN)(atN)(atN)(atN)(atN)*N.

The kit may further comprise reagents or reagent solutions required for performing a nucleic acid amplification reaction. It may further include an instruction manual detailing the specific components included in the kit, or the methods for using them in nucleic acid amplification reactions, or both.

The following examples are offered by way of illustration and not by way of limitation:

EXAMPLES

Example 1

Improvement in MDA Speed and Sensitivity

Amplification reactions were performed using the standard GenomiPhi™ kit with the hexamer sequence NNNN*N*N and 75 mM KCl or utilizing the "cleaned" GenomiPhi (see, for example, U.S. Patent Application Publication No. 2009/0155859), GenomiPhi SD (e.g., U.S. Pat. No. 7,993,839), or GenomiPhi AT formulations. Real-time amplification was performed by adding a small amount of SYBR green I to the amplification mixture and monitoring fluorescence increase over time in a Tecan plate reader using a dilution series of Bacillus subtilis chromosomal DNA. A no template control was also analyzed (NTC).

Figure 3A:
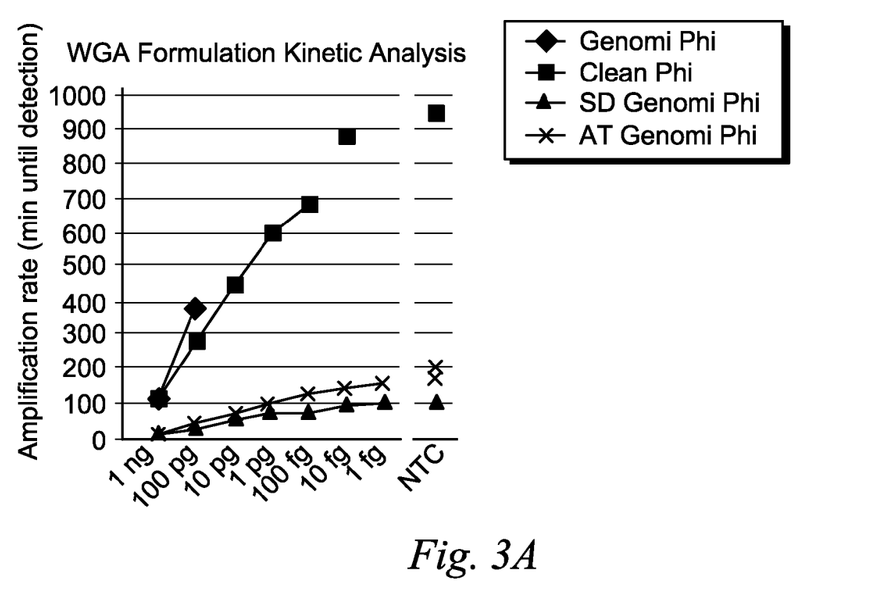
FIG. 3A provides the results of amplification reactions of dilution series of *Bacillus subtilis* chromosomal DNA or a no nucleic acid control (NTC) that were performed using the standard GenomiPhi™ kit or utilizing the "cleaned" GenomiPhi, SD GenomiPhi, or AT GenomiPhi formulations. The threshold time for DNA amplification signal to increase over background for each reaction was plotted out versus the amount of DNA added as input template into the reaction.
Figure 3B:
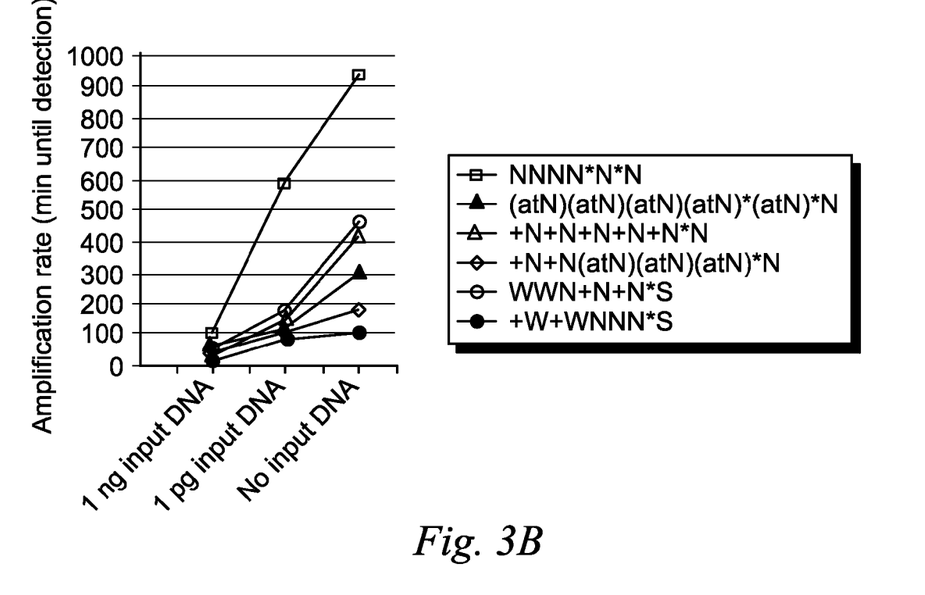
FIG. 3B provides the results of amplification reactions of *Bacillus subtilis* chromosomal DNA that were performed using the standard GenomiPhi™ kit using the hexamer sequence NNNN*N*N and 75 mM KCl, the "cleaned" GenomiPhi SD, or the GenomiPhi AT formulations, as described herein above. A no template control was also performed (NTC). Details are set forth in Example 1.

The threshold time for DNA amplification signal to increase over background for each reaction was plotted out versus the amount of DNA added as input template into the reaction. Reactions containing primers with LNA and amino-A/thio-T showed an approximately 10 fold increase in amplification kinetics. The results are summarized in FIGS. 3A and 3B.

Example 2

Figure 4A:
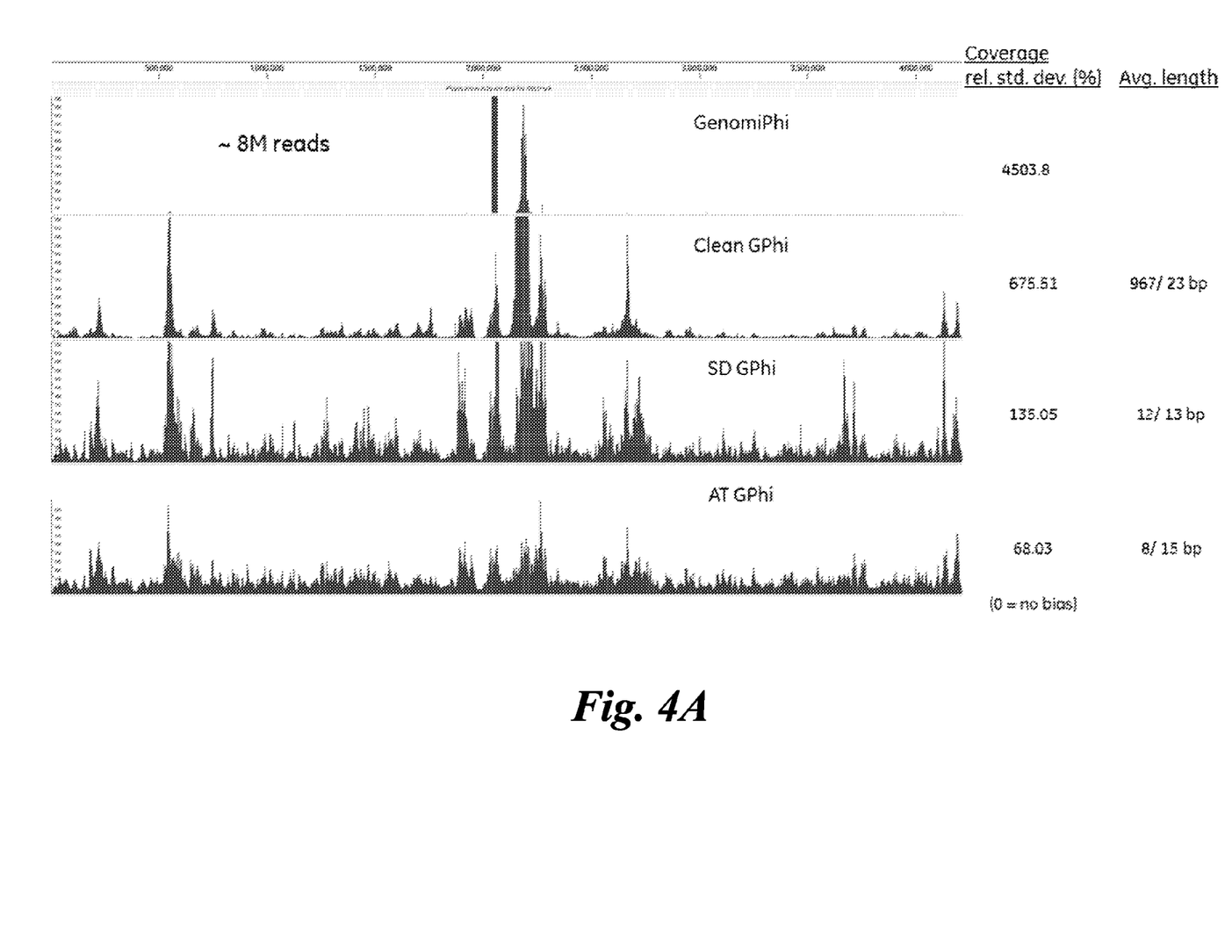
Figure 4B:
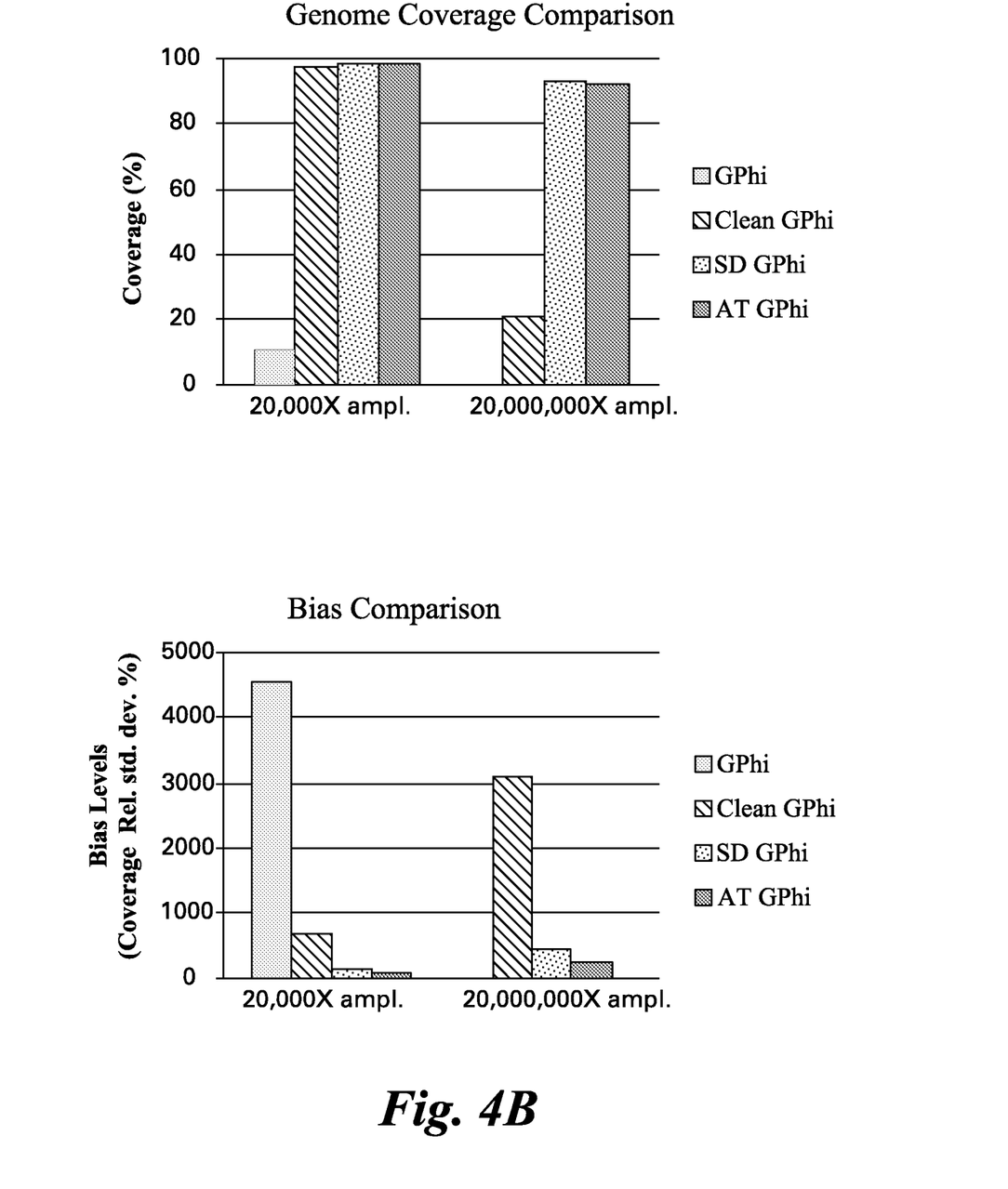
FIG. 4B summarizes the data in bar graph format.

Oligonucleotides Containing 2-Amino-dA and 2-Thio-dT Improve MDA Coverage and Overall Amplification Bias Standard GenomiPhi™ reactions or MDA reactions with the indicated formulations were performed with 100 pg B. subtilis input DNA. Total amplification in the reactions was approximately 20.000-fold. Amplified DNA was processed into libraries and subjected to Illumina GA whole-genome sequencing with a 51 nucleotide read length. 8-10 million reads for each sample were mapped to the B. subtilis reference genome. FIG. 4A provides a histogram that maps coverage level across the length of the genome. Relative standard deviations were calculated by the following formula: coverage standard deviation/mean coverage*100. The number of coverage gaps and the average lengths of those gaps are also indicated. FIG. 4B provides bar graphs comparing the formulations.

Example 3

Oligonucleotides Containing 2-Amino-dA and 2-Thio-dT Improve MDA Sequence Bias

Figure 5:
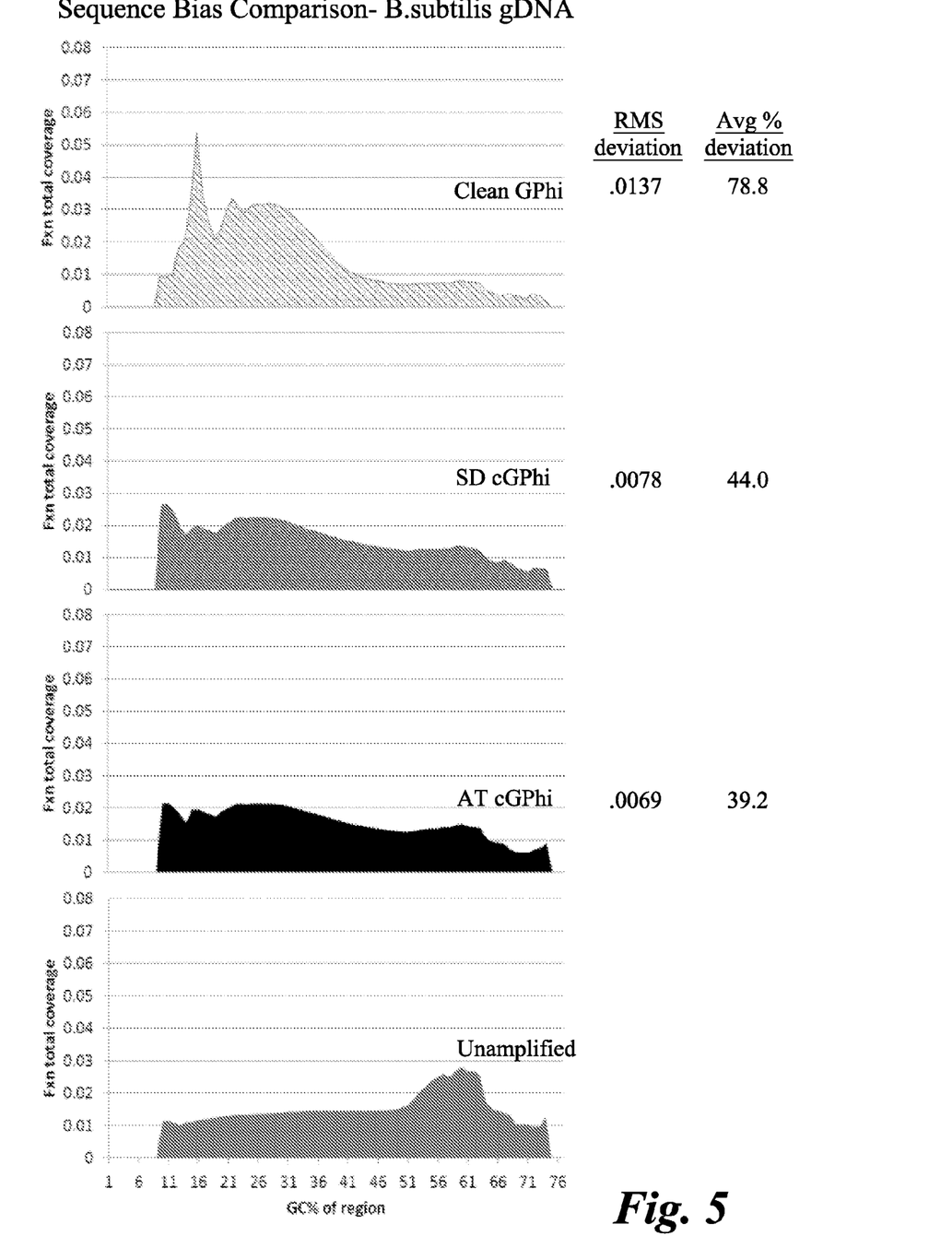
FIG. 5 provides the coverage level determined for each 100 base pair window of the genome and GC content of windows or the amplification reactions in FIG. 2. The coverage level was plotted against the fractional coverage of windows that had that GC content. Details of this example are set forth below in Example 3.

For the amplification reactions described in Example 3, the coverage level was determined for each 100 base pair window of the genome. GC content of the windows was plotted against the fractional coverage of windows that had that GC content. The results are presented in FIG. 5 and indicate that the inclusion of amino-A/thio-T and LNA nucleotides in the amplification primer provide both increased representative amplification and decreased amplification bias.

Example 4

Amplification of Single Bacterial Cells Using the GenomiPhi AT Formulation

Figure 6A:
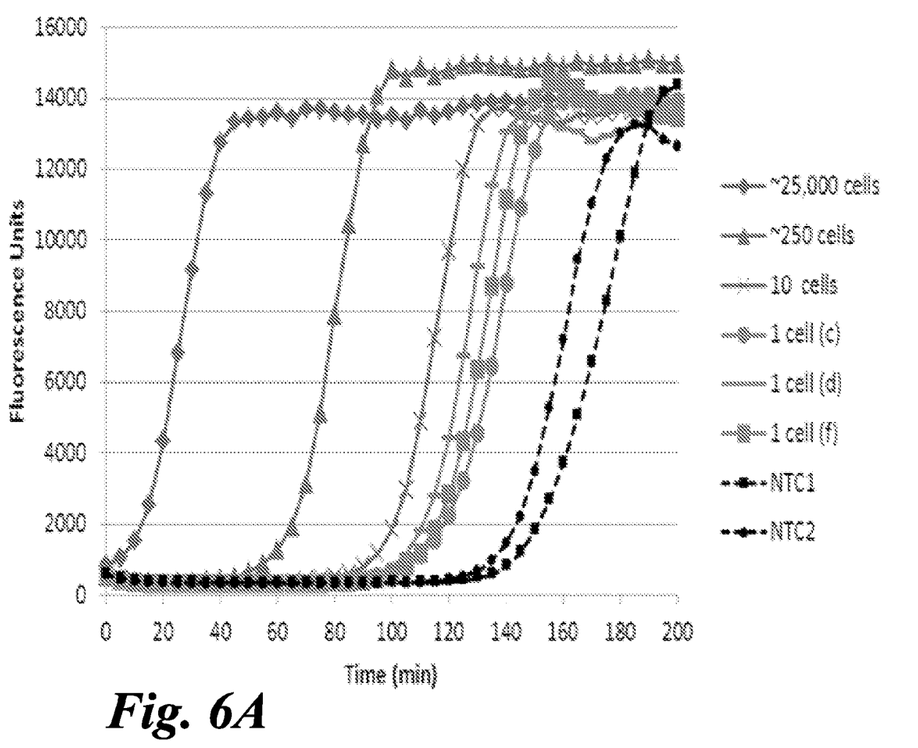
FIG. 6A provides the results from amplification reactions of *E. coli* chromosomal DNA performed using the improved AT GenomiPhi method. A no template control was also performed (NTC). Additional details are set forth in Example 4.

Amplification reactions were performed using the improved GenomiPhi AT formulation. Real-time amplification was performed by adding a small amount of SYBR green I to the amplification mixture and monitoring fluorescence increase over time in a Tecan plate reader. E. coli cells were diluted with a buffer containing 10 mM Tris, pH 7.5, 100 mM NaCl, and 0.1 mM EDTA, stained with FM1-43FX dye (Invitrogen), spotted into wells of a 384-well plate, and cells were counted using an inverted Fluorescent microscope (Nikon). Cells were lysed by addition of 1 µl of 0.2 M NaOH, 0.015% Tween-20, incubated for 10 min at room temperature, and neutralized by addition of 0.5 µl of 0.4 M HCl, 0.6 M Tris, pH 7.5. To this mixture was added the amplification reagents and reactions were incubated at 30° C. for the indicated times. A no template control was also analyzed (NTC). The results are summarized in FIG. 6A.

Figure 6B:
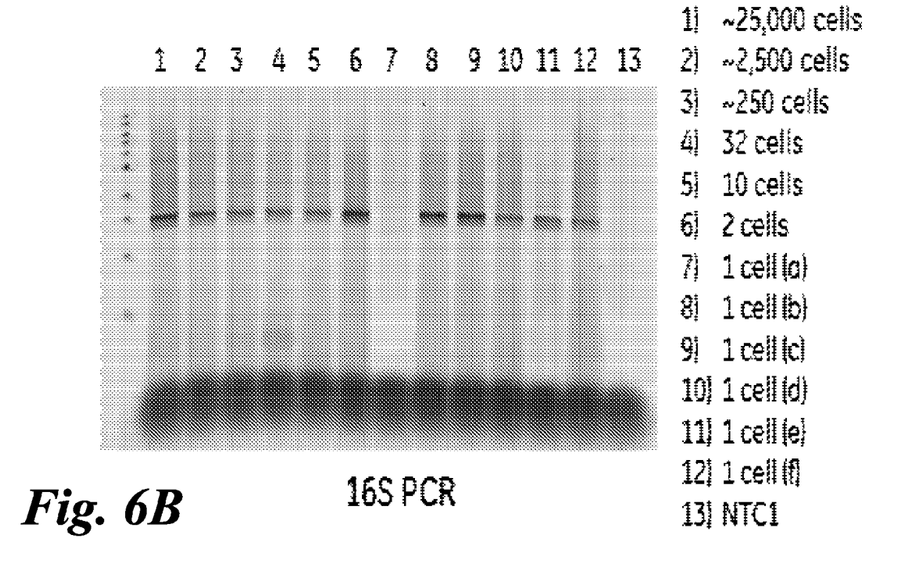
FIG. 6B summarizes the analysis of performed by PCR.

PCR was performed using 16S ready-made primers (NEB) and Amplitaq Gold reagents (Invitrogen) according to the manufacturer's instructions. DNA was analyzed by 1% agarose gel electrophoresis, stained with SYBR gold (Invitrogen), and visualized by scanning with a Typhoon imager (GE Healthcare). See FIG. 6B.

Figure 6C:
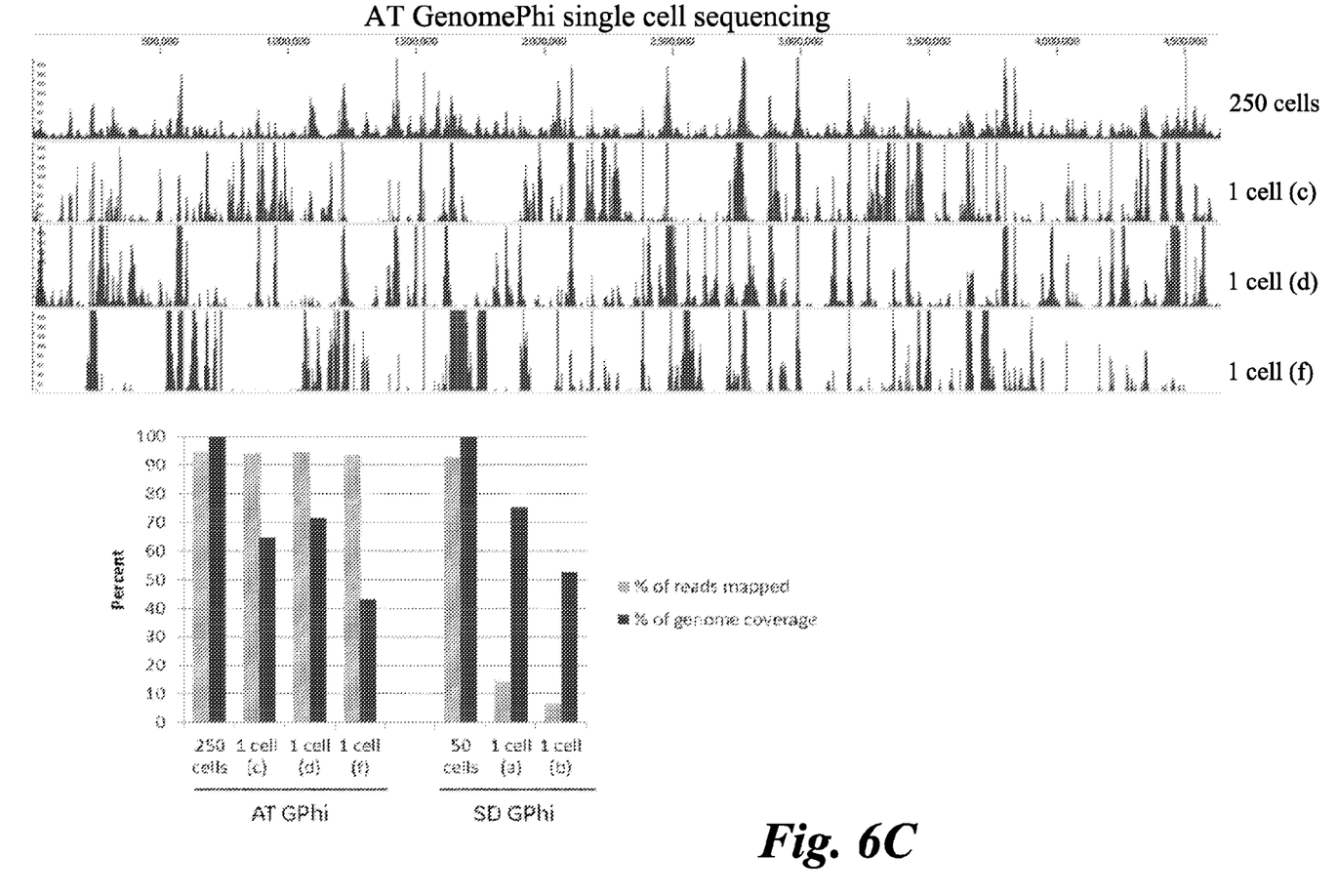
FIG. 6C provides a histogram of coverage levels, the percent of reads mapped, and genome coverage levels. Experimental details are disclosed in Example 4.

Amplified DNA was processed and subjected to Illumina GA whole-genome sequencing as described above. A histogram of coverage levels, the percent of reads mapped, and genome coverage levels are plotted in FIG. 6C.

All publications, patents, and patent applications mentioned herein are incorporated by reference in their entirety to the same extent as if each individual publication, patent, or patent application was specifically and individually indicated to be incorporated by reference.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A method for amplifying a nucleic acid comprising:
a) providing a nucleic acid template;
b) contacting the nucleic acid template with a reaction solution comprising a DNA polymerase, deoxyribo- nucleoside triphosphates, and a primer with a 3' end and a 5' end, wherein the primer comprises a plurality of nucleotide analogues, wherein one or more nucleotide analogues of the plurality of nucleotide analogues increases the melting temperature ($T_m$) of the primer, one or more nucleotide analogues of the plurality of nucleotide analogues prevents primer-dimer formation, and at least two nucleotide analogues of the plurality of nucleotide analogues are not a 2-amino-locked nucleic acid (LNA) nucleotide or a 2-thio-LNA nucleotide, and wherein one of the nucleotide analogues is 2-amino-deoxyadenosine (2-amino-dA) and one of the nucleotide analogues is 2-thio-deoxythymidine (2-thio-dT), and the 2-amino-dA increases the $T_m$ of the primer and both the 2-amino-dA and the 2-thio-dT prevent primer-dimer formation, and wherein the primer is a hexamer having the general structure of (+N)(+N)(atN)(atN)(atN)*N, wherein N represents a nucleotide having a nucleobase of cytosine, guanine, adenine, or thymine, wherein (+N) is the 5' end nucleotide and *N is the 3' end nucleotide of the hexamer, and wherein "+" indicates an LNA that precedes a nucleotide base, (atN) represents a random mixture of 2-amino-dA, deoxycytidine (dC), deoxyguanosine (dG), and 2-thio-dT, and "*" represents a phosphorothioate linkage; and c) amplifying the nucleic acid template.

2. The method of claim 1, wherein amplifying the nucleic acid template is performed under isothermal conditions.

3. The method of claim 1, wherein amplifying the nucleic acid template is performed under high stringency conditions.

4. The method of claim 1, wherein the DNA polymerase is phi29 DNA polymerase.

5. The method of claim 1, wherein amplifying the nucleic acid template comprises a rolling circle amplification (RCA) or a multiple displacement amplification (MDA).

6. The method of claim 1, wherein the method permits amplification of a trace amount of the nucleic acid.

* * * * *